United States Patent
Le Guillou et al.

(10) Patent No.: US 12,274,534 B2
(45) Date of Patent: Apr. 15, 2025

(54) MONITORING DEVICE FOR MONITORING A PHYSIOLOGICAL PARAMETER AND METHODS THEREOF

(71) Applicant: BIOSENCY, Saint-Grégoire (FR)

(72) Inventors: Yann Le Guillou, Rennes (FR); Quentin Bodinier, Rennes (FR)

(73) Assignee: BIOSENCY, Saint-Grégoire (FR)

( * ) Notice: Subject to any disclaimer, the term of this patent is extended or adjusted under 35 U.S.C. 154(b) by 641 days.

(21) Appl. No.: 16/967,261

(22) PCT Filed: Feb. 15, 2019

(86) PCT No.: PCT/EP2019/053841
§ 371 (c)(1),
(2) Date: Aug. 4, 2020

(87) PCT Pub. No.: WO2019/158704
PCT Pub. Date: Aug. 22, 2019

(65) Prior Publication Data
US 2020/0367764 A1    Nov. 26, 2020

(30) Foreign Application Priority Data
Feb. 15, 2018  (EP) .................................... 18305156

(51) Int. Cl.
*A61B 5/00*   (2006.01)
*A61B 5/0205*  (2006.01)
(Continued)

(52) U.S. Cl.
CPC ........ *A61B 5/02055* (2013.01); *A61B 5/0205* (2013.01); *A61B 5/14551* (2013.01);
(Continued)

(58) Field of Classification Search
CPC . A61B 5/1118; A61B 5/02416; A61B 5/0816; A61B 5/0205; A61B 2562/0219
See application file for complete search history.

(56) References Cited

U.S. PATENT DOCUMENTS

| | | | |
|---|---|---|---|
| 6,506,153 B1 | 1/2003 | Littek et al. | |
| 2006/0122476 A1 | 6/2006 | Van Slyke | |

(Continued)

FOREIGN PATENT DOCUMENTS

| | | |
|---|---|---|
| EP | 2 987 453 A1 | 2/2016 |
| EP | 2 755 551 B1 | 8/2016 |

OTHER PUBLICATIONS

Ja-Woong Yoon et al. (2014) "Improvement of Dynamic Respiration Monitoring Through Sensor Fusion of Accelerometer and Gyro-sensor," J Electr Eng Technol vol. 9, No. 1: 334-343, 2014. The Korean Institute of Electrical Engineers. doi: 10.5370/jeet.2014.9.1.334.*

(Continued)

*Primary Examiner* — Lynsey C Eiseman
*Assistant Examiner* — James Moss
(74) *Attorney, Agent, or Firm* — Maier & Maier, PLLC

(57) ABSTRACT

A method to process signals acquired with at least one accelerometer and one gyroscope worn by a subject for evaluating a heart rate and/or a respiratory rate. The method includes: receiving the accelerometer and gyroscope signals at a sampling frequency in a given time window; combining each pair of accelerometer and gyroscope signals in the given window to output an orientation vector for each sampling time using a quaternion representation; applying at least one filter to the orientation signal defined by the orientation vectors to obtain a filtered signal; calculating an average breath cycle and/or time interval separating two consecutive heart beats using an algorithm for modeling an average signal, which iteratively determines the average (Continued)

between the filtered signal and the average signal from a preceding iteration; estimating a heart and/or respiratory rate from the calculated average breath cycle and/or time interval separating two consecutive heart beats.

17 Claims, 4 Drawing Sheets

(51) Int. Cl.
  *A61B 5/1455* (2006.01)
  *A61B 5/024* (2006.01)
  *A61B 5/08* (2006.01)

(52) U.S. Cl.
  CPC ............ *A61B 5/721* (2013.01); *A61B 5/7221* (2013.01); *A61B 5/7225* (2013.01); *A61B 5/7278* (2013.01); *A61B 5/02416* (2013.01); *A61B 5/02438* (2013.01); *A61B 5/0816* (2013.01); *A61B 2562/0219* (2013.01)

(56) References Cited

U.S. PATENT DOCUMENTS

| | | | |
|---|---|---|---|
| 2007/0088221 A1 | 4/2007 | Stahmann | |
| 2014/0275852 A1* | 9/2014 | Hong | A61B 5/0002 600/479 |
| 2015/0335288 A1* | 11/2015 | Toth | A61B 5/6833 600/391 |
| 2015/0351690 A1* | 12/2015 | Toth | A61B 5/6839 600/391 |
| 2016/0058375 A1* | 3/2016 | Rothkopf | G04G 17/02 600/323 |
| 2016/0360977 A1 | 12/2016 | Salehizadeh et al. | |
| 2017/0128020 A1* | 5/2017 | Olivier | A61B 5/721 |
| 2019/0133499 A1* | 5/2019 | Auerbach | A61B 5/1135 |
| 2019/0313947 A1* | 10/2019 | Li | A61B 5/067 |
| 2020/0260962 A1* | 8/2020 | Mouchantaf | A61B 5/4809 |

OTHER PUBLICATIONS

InvenSense, MPU-6000 and MPU-6050 Product Specification Revision 3.4, Aug. 19, 2013, viewed on Nov. 19, 2022.*
InvenSense, Motion Sensors Introduction, Jun. 26, 2012, https://www.cdiweb.com/datasheets/invensense/sensor-introduction.pdf, viewed on Nov. 17, 2022.*
International Search Report and Written Opinion of the International Searching Authority issued on May 10, 2019 in corresponding International application No. PCT/EP2019/053841; 13 pages.
Hernandez et al., "Biowatch: Estimation of heart and breathing rates from wrist motions", 2015 9th International Conference on Pervasive Computing Technologies for Healthcare, 2015, pp. 169-176; 8 pages.
Williamson et al., "Data sensing and analysis: Challenges for wearables", The 20th Asia and South Pacific Design Automation Conference, 2015, pp. 136-141; 6 pages.
Yang et al., "Collective sensing of workers' gait patterns to identify fall hazards in construction", Automation in Construction, 2017, pp. 166-178, vol. 82; 13 pages.
Sharifahmadian et al., "Adaptive signal processing algorithm for remote detection of heart rate (HR) using ultra-wideband waveforms based on principal component analysis", Engineering the Future of Biomedicine, 2009, pp. 5717-5720; 4 pages.
Liu et al., "Estimation of Respiration Rate from Three-Dimensional Acceleration Data Based on Body Sensor Network", Telemedicine and E-Health, 2011, pp. 705-711, vol. 17; 7 pages.
Haescher et al., "SmartMove: A Smartwatch Algorithm to Distinguish Between High- and Low-Amplitude Motions as well as Doffed-States by Utilizing Noise and Sleep", Sensor-Based Activity Recognition and Interaction, 2016, pp. 1-8; 8 pages.
Lowe et al., "Monitoring human health behaviour in one's living environment: A technological review", Medical Engineering & PHYSICS, 2013, pp. 147-168, vol. 36; 22 pages.
Shen et al., "Respiratory Rate Estimation by Using ECG, Impedance, and Motion Sensing in Smart Clothing", Journal of Medical and Biological Engineering, 2017, pp. 826-842, vol. 37; 17 pages.
Hernandez et al., "Respiratory effort monitoring system for sleep apnea screening for both supine and lateral recumbent positions", Electronics and Mobile Communication Conference, 2017, pp. 191-197; 7 pages.

* cited by examiner

MONITORING DEVICE FOR MONITORING A PHYSIOLOGICAL PARAMETER AND METHODS THEREOF

FIELD

The present invention pertains to the field of monitoring of physiological signal in a subject. In particular, the invention relates to a monitoring device configured to measure the heart rate and the breath rate in a subject and the methods thereof.

BACKGROUND

In recent years, the interest in population health and well-being has grown tremendously. This growth is the consequence of a better understanding of the benefits of good fitness to overall health and wellness. To provide users or medical professionals concerned with their health or their patients' health a way of measuring or accounting for physiological signals during the daily activity, fitness trackers are often used. Fitness trackers are used to measure activity, such as walking, motion, running and the like; and at the same time some physiological parameters such as respiratory rate and heart rate.

Several fitness trackers are known from the prior art, such as the portable devices disclosed by the European patent applications EP 2 755 551 and EP 2 987 453. Such portable devices comprise a heart rate measuring unit comprising a PPG sensor for measuring a blood pulse wave of the person over time to generate the heart rate signal, and a motion measurement unit comprising an accelerometer and/or a gyroscope for measuring an acceleration of the body part. However, these patent applications disclose devices configured to monitor only the heart rate of the subject. Furthermore, PPG sensors are particularly energy consuming sensors which therefore drastically reduce the autonomy time of such portable devices.

SUMMARY

The present invention relates to a method to process signals acquired with at least one accelerometer and one gyroscope for the evaluation of a heart rate and/or a respiratory rate of a subject wearing said accelerometer and said gyroscope, said method comprising the following steps:
  reception of the signals acquired with a predefined sampling frequency by the accelerometer and the gyroscope in a given time window;
  for each corresponding pair of samples of signals acquired by the accelerometer and the gyroscope in the given time window, combination of the samples of signals of the accelerometer and the gyroscope so as to output an orientation vector for each sampling time using a quaternion representation;
  application of at least one filter to the orientation signal defined by the orientation vectors obtained for the sampling times in the given time window so as to obtain a filtered signal;
  calculating an average breath cycle and/or an average time interval separating two consecutive heart beats using an algorithm for modeling an average signal configured to iteratively determine the average between the filtered signal obtained for the given time window and the average signal obtained in a preceding iteration for a preceding time window;
  estimation of a heart rate and/or a respiratory rate from the average breath cycle and/or the average time interval separating two consecutive heart beats calculated.

A great advantage of quaternions representation over other approaches known by the skilled artisan is their relative computational simplicity which translates in increased power efficiency. Furthermore, the quaternion representation has the advantage of performing an analysis on a signal that is truly representative of the movement of the inertial motion unit rather than on an arbitrary axis as a function of time, largely improving the quality of the obtained results as it allows to observe the main direction of the movements.

The implementation of an algorithm for modeling an average signal provides an accurate approach in which the method iteratively models the average signal as precisely as possible. This advantageously allows a more effective demodulation of the input signal.

According to one embodiment, the method further comprises a step of estimation of a quality metrics related to the accuracy of the heart rate and/or the respiratory rate estimated and a step of calculation of filter coefficients of the at least one filter on the basis of said quality metrics.

According to one embodiment, the average breath cycle and/or the average time interval separating two consecutive heart beats are further calculated using at least one computation algorithm chosen from a list comprising at least a direct frequency estimation algorithm and a blind equalization algorithm, the selection of the computation algorithm being made on the basis of at least one first indicator calculated from said quality metrics.

According to one embodiment, the filtering step comprises the application of two band pass filters optimized according to a Parks-McClellan method.

This approach has the advantage of providing shorter filters satisfying the desired frequency mask to isolate the heart rate and respiratory rate components in the most efficient way, which makes it possible to filter the accelerometer and gyroscope signals in real time.

The global advantage provided by the particular selection of the consecutive steps of the method of the present invention is that of providing a technical solution allowing the execution of signal processing algorithms in electronic systems having limited computational performances, as the ones that may be integrated in portable monitoring devices as the ones described here below.

According to one embodiment, the step of application of the at least one filter comprises:
  filtering the orientation signal in the band [0.08 Hz; 0.5 Hz] for selecting a part of the orientation signal comprising at least partially the breath activity;
  filtering the orientation signal in the band [0.5 Hz; 4 Hz] for selecting a part of the orientation signal comprising at least partially the heart activity.

According to an alternative embodiment, the method of the present invention is configured to process signals acquired with at least one accelerometer and one gyroscope for the evaluation of a heart rate and/or a respiratory rate of a subject wearing said at least one accelerometer and said at least one gyroscope, said method comprising the following steps:
  reception of the signals acquired by the at least one accelerometer and the at least one gyroscope;
  combination of the signals acquired by the at least one accelerometer and the at least one gyroscope outputting an orientation vector using a quaternion representation;

application of at least one filter to the orientation vector obtaining a filtered signal;

calculating a breath cycle and/or a time interval separating two consecutive heart beat according to at least one selection of at least one computation algorithm according to at least one first indicator;

estimation of a heart rate and/or a respiratory rate from the breath cycle and/or the time interval separating two consecutive heart beat calculated;

estimation of a quality metrics related to the accuracy of the heart rate and/or the respiratory rate estimated, the first indicator being calculated on the basis of said quality metrics.

According to one embodiment, the selection of one computation algorithm is performed according to a plurality of algorithms comprising at least: a direct frequency estimation algorithm, a signal modeling algorithm and a blind equalization algorithm.

According to one embodiment, the filter coefficients of at least one filter are calculated on the basis of said quality metrics.

According to one embodiment, the filtering step comprises the application of two band pass filters optimized according to a Parks-McClellan method.

According to one embodiment, the method comprises a filtering step comprising:

filtering the signal in the band [0.08 Hz; 0.5 Hz] for selecting a part of the signal comprising at least partially the breath activity;

filtering the signal in the band [0.5 Hz; 4 Hz] for selecting a part of the signal comprising at least partially the heart activity.

The present invention further relates to a method to evaluate a heart rate and/or a respiratory rate of a subject wearing a monitoring device comprising at least one accelerometer, at least one gyroscope and at least one photoplethysmograph, wherein said method comprises the following steps:

estimating a level of activity of the subject according to signals acquired by the at least one accelerometer and the at least one gyroscope;

comparing said level of activity to a predefined threshold;

activating the photoplethysmograph when the level of activity is above the predefined threshold and calculating the heart rate and/or the respiratory rate using the photoplethysmographic signal; or disactivating the photoplethysmograph when the level of activity is below the predefined threshold and implementing the method to process signals acquired with at least one accelerometer and one gyroscope according to anyone of the embodiment described hereabove.

According to one embodiment, the photoplethysmograph is periodically activated and the heart rate and/or the respiratory rate estimated with the PPG signal are used to evaluate the heart rate and/or the respiratory rate obtained signals acquired with at least one accelerometer and one gyroscope.

According to one embodiment, the difference between the heart rate and/or the respiratory rate obtained from the photoplethysmographic signal and the at least one accelerometer and one gyroscope signals is used as feedback signal for the calculation of the filter coefficients.

According to one embodiment, the method of the present invention further comprises a step for removing a motion artefact from the photoplethysmographic signal. The present invention further relates to a monitoring device for monitoring a physiological parameter of a subject wearing said monitoring device, comprising:

a photoplethysmograph, to measure oxygen saturation in blood in order to detect a frequency related to hearth rate and respiratory rate;

an inertial motion unit comprising at least one gyroscope and/or at least one accelerometer; and a processor configured to implement the following steps:

measuring a level of activity of the subject according to signals acquired by the at least one accelerometer and the at least one gyroscope;

comparing said level of activity to a second indicator;

activating the photoplethysmograph when the level of activity is above a predefined threshold and calculating the heart rate and/or the respiratory rate using the photoplethysmographic signal; or disactivating the photoplethysmograph and implementing the method to process signals acquired with at least one accelerometer and one gyroscope according to anyone of the embodiment described hereabove.

According to one embodiment, the monitoring device further comprising a temperature sensor.

The present invention further relates to a monitoring device for monitoring a physiological parameter, comprising:

a photoplethysmograph, to measure oxygen saturation in blood in order to detect a frequency related to hearth rate and respiratory rate;

an inertial motion unit comprising at least one gyroscope and/or at least one accelerometer; and a processor configured to implement the method according to anyone of the embodiment described hereabove.

According to one embodiment, the data acquired and/or processed by the monitoring device are transmitted to a server operating system.

The advantage of a monitoring device and methods of the present invention, is that of allowing the monitoring of heart rate and respiratory rate of a subject over extended time periods (i.e. from a few hours to a few days) thanks to the energy saving methods implemented.

Definitions

In the present invention, the following terms have the following meanings:

As used herein the singular forms "a", "an", and "the" include plural reference unless the context clearly dictates otherwise.

The term "about" is used herein to mean approximately, roughly, around, or in the region of. When the term "about" is used in conjunction with a numerical range, it modifies that range by extending the boundaries above and below the numerical values set forth. The term "about" is used herein to modify a numerical value above and below the stated value by a variance of 20 percent, preferably of 5 percent.

"Photoplethysmograph" or "PPG sensor" refers to an optically obtained plethysmogram, which performs a volumetric measurement of an organ. In a PPG, the changes in volumes caused by pressure pulses are detected by illuminating the skin of a subject with the light from a light-emitting diode (LED) and then measuring the amount of light either transmitted or reflected to a photodiode.

"Physiological signal" refers herein to any signal in subjects that can be continually measured and monitored. Physiological signal refers especially to any biological parameter which can be measured by an instrument which converts a physical measure (light, pressure, electricity, radio-signal . . . ) into an analogous signal (in volts, amperes, etc.).

"Subject" refers to a mammal, preferably a human. In the sense of the present invention, a subject may be a patient, i.e. a person receiving medical attention, undergoing or having underwent a medical treatment, or monitored for the development of a disease.

"$SpO_2$" or "oxygen saturation" refers to the fraction of oxygen-saturated hemoglobin relative to total hemoglobin (unsaturated plus saturated) in the blood.

DETAILED DESCRIPTION

The following detailed description will be better understood when read in conjunction with the drawings. For the purpose of illustrating, the device and the succession of instructions implemented by the methods are shown in the preferred embodiments. It should be understood, however, that the application is not limited to the precise arrangements, structures, features, embodiments, and aspect shown. The drawings are not drawn to scale and are not intended to limit the scope of the claims to the embodiments depicted. Accordingly, it should be understood that where features mentioned in the appended claims are followed by reference signs, such signs are included solely for the purpose of enhancing the intelligibility of the claims and are in no way limiting on the scope of the claims.

A first aspect of the present invention relates to a method to process signals acquired with at least one accelerometer $S_a$ and at least one gyroscope $S_g$. In the scope of the invention, the acquired signals allow evaluating a heart rate HR and/or a respiratory rate RR of a subject wearing said at least one accelerometer and said at least one gyroscope. According to one embodiment, said at least one accelerometer and one gyroscope are comprised in a monitoring device which may be adapted to be worn or carried on the body of a user. In some embodiments, said monitoring device is a wrist-worn or an arm-mounted accessory such as a watch or a bracelet. In one embodiment, the at least one accelerometer and one gyroscope are embedded in an inertial motion unit (IMU) which may be comprised in the monitoring device. In the following description, the inertial motion unit signal is used as equivalent to the signals acquired with at least one accelerometer $S_a$ and one gyroscope $S_g$.

Figure 1:
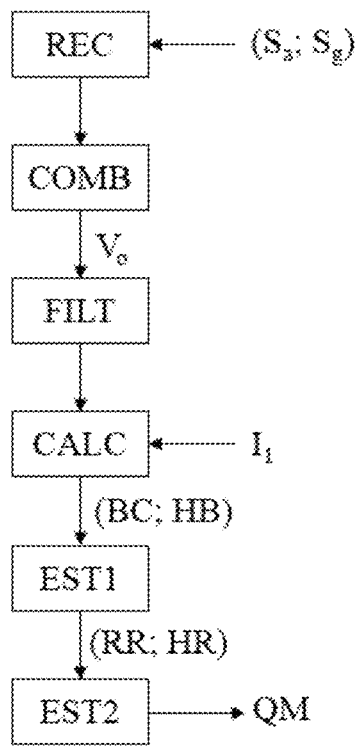
FIG. 1 is a flow chart showing the main steps of the method to process signals acquired with at least one accelerometer $S_a$ and at least one gyroscope $S_g$ for the evaluation of a heart rate HR and/or a respiratory rate RR of a subject wearing said at least one accelerometer $S_a$ and at least one gyroscope $S_g$, according to one embodiment of said method.

As illustrated in FIG. 1 according to one embodiment, said method comprises a preliminary step REC consisting in the reception of the signals acquired by the at least one accelerometer $S_a$ and the at least one gyroscope $S_g$ acquired with a predefined sampling rate. In one alternative embodiment, said preliminary step further consists in the acquisition of the signals of the at least one accelerometer $S_a$ and the at least one gyroscope $S_g$ with a predefined sampling rate. Notably the sampling of the accelerometer signal $S_a$ and gyroscope signal $S_g$ is synchronous. In one example, the sampling rate may have a value ranging from 10 Hz to 60 Hz. According to one embodiment, the method is configured to sequentially analyze the incoming signals in a given time window of predefined length, notably of a few seconds in order to comprise at least two heart beat and/or respiratory cycles. Said time window may extend for example between the time t minus 2 seconds and the time t. In a preferred example, the successive time windows do not overlap.

According to one embodiment, in a following step COMB of the present method the accelerometer signal $S_a$ and gyroscope signal $S_g$ are represented in an alternative referential such as for example a quaternion referential. According to one embodiment, the accelerometer signal $S_a$ and gyroscope signal $S_g$ are combined using a quaternion representation. According to this embodiment, the method of the present invention comprises a quaternion computation stage which outputs an orientation vector $V_o$ for each sampling time $t_s$ associated to a pair of measures of the accelerometer signal $S_a$ and gyroscope signal $S_g$. Therefore, this step of the method provides a set of n orientation vector $V_o$, where n is the number of samples of the signals performed in the given time window analyzed. This step allows an accurate measure of the temporal evolution of the position of the monitoring device during at least one heart beat and/or respiratory cycle. This step has the advantage of performing an analysis on a signal that is truly representative of the movement of the inertial motion unit rather than on an arbitrary axis as a function of time. In particular, this combination will largely improve the obtained results quality as it allows to observe the main direction of the movements, even in cases where it does not correspond to a particular axis of the at least one accelerometer or the at least one gyroscope. Furthermore, a great advantage of quaternions representation over other approaches known by the skilled artisan is their relative computational simplicity which translates in increased power efficiency. Contrary to the use of a vector norm for the combination of multiple components of a signal, which is known to the person skilled in the art, the implantation of quaternion is an advantageous alternative to this known solution, allowing to overcome the main drawbacks of using the norm of the accelerometer signal and/or gyroscope signal (i.e. loss of information concerning the direction of the movement generating the signal).

According to one embodiment, the method of the present invention further comprises a filtering step FILT. Said step consists in the application of at least one filter to orientation signal defined by the orientation vectors $V_o$ obtained for the sampling times in the given time window so as to obtain a filtered signal. In some embodiments, the orientation vectors $V_o$ are filtered by two different pass-band filters. Said pass-band filters are used in order to isolate the part of orientation signal that contains the low frequency respiration signal on the one hand and the high frequency pulse signal on the other hand. In one embodiment, those frequency band are exclusive of each other's. According to one embodiment, the pass-band filter for selecting a part of the orientation signal comprising at least partially the breath activity is defined in the band [0.08 Hz; 0.5 Hz] and the band-pass filter for selecting a part of the orientation signal comprising at least partially the heart activity is defined in the band [0.5 Hz; 4 Hz]. In one embodiment, the pass-band filter for selecting a part of the orientation signal comprising at least partially the breath activity is defined in the band [0.08 Hz; 0.25 Hz]. In one embodiment, the band-pass filter for selecting a part of the orientation signal comprising at least partially the heart activity is defined in the band [1 Hz; 4 Hz]. In one embodiment, the two band-pass filters have an optimized design. In one preferred embodiment, the filters design is optimized using the Parks-McClellan method which is an iterative algorithm allowing to find the optimal Chebyshev finite impulse response filter by calculation of optimal filter coefficients. This optimization approach is clearly more advantageous than the simple choice of coefficients from a look-up table as a function of the characteristics of the signal. This approach has the advantage of providing shorter filters satisfying the desired frequency mask to isolate the heart rate HR and respiratory rate RR components in the most efficient way, which makes it possible to filter the inertial motion unit IMU signal in real time. Obtaining shorter filters using the Parks-McClellan method has the further advantage of reducing the complexity of the filtering computation so as to obtain less computational time (i.e. consuming less CPU power). In an alternative embodiment, the filters are designed to be Butterworth band-pass filtered with preset gains. In another alternative embodiment, the filters are set to have a rejection of at least 40 dB outside of the bands of interest. In other embodiments, the level of rejection is set in the band [10 dB; 60 dB] according to the level of noise detected outside of the bands of interest.

According to an alternative embodiment, the filtering step is performed directly on the raw signal of the accelerometer $S_a$ and the gyroscope $S_g$ received in the first step of the method.

In one embodiment, the method according to the first aspect of the present invention comprises a step of calculation of a breath cycle. In one embodiment, the method according to the first aspect of the present invention comprises also a step of calculation of a time interval separating two consecutives heart beats. This calculation step CALC comprises calculating the breath cycle BC and/or the time interval separating two consecutives heart beats HB on each of the axis of the orientation vector. According to one embodiment, for this computational step, the at least one computation algorithm is selected according to at least one first indicator $I_1$. According to one embodiment, the first indicator $I_1$ is extracted from a quality metric QM directly related to the quality of the signal estimation.

According to one embodiment, the at least one computation algorithm is selected from a library comprising a plurality of algorithms Said library comprises at least a direct frequency estimation algorithm, a modeling of the average signal algorithm and a blind equalization algorithm. In one embodiment, the blind equalization algorithm relies on a Maximum A Posteriori (MAP) estimation technique to estimate the most likely shape of a heart beat and/or respiratory cycle. Said library may further comprise frequency estimation algorithms based on Energy Detection (ED) techniques and/or cyclo-stationarity estimation algorithms based on the detection of cyclic signatures in the heart and respiratory signals.

According to a preferred embodiment, the calculation step CALC estimates the average breath cycle BC and/or the average time interval separating two consecutives heart beats HB using the algorithm for modeling an average signal. Indeed, this algorithm allows a more precise approach in which the method iteratively models the average signal as precisely as possible. This advantageously allows a more effective demodulation of the input signal. More in details, this algorithm is configured to first detect the signal corresponding to each heart beat and respiratory cycle on each time window. Then, the signal corresponding to each heart beat or respiratory cycle is used as an input to an arithmetic means between the new average signal obtained from the filtered signal and an estimation of the average signal obtained in a previous iteration of the present method. The weights used may be fixed or adapted to the nature of the incoming signal (i.e. signal to noise ratio of the signal in the time window analyzed).

According to on embodiment, in addition to the algorithm for modeling an average signal, one or more algorithms are selected from the library and executed in parallel to obtain multiple estimations of the average breath cycle BC and/or the average time interval separating two consecutives heart beats HB so as to improve the accuracy of the method. This selection is done according to the value of the first indicator $I_1$.

According to alternative embodiment, the default algorithm used to estimate the average breath cycle BC and/or the average time interval separating two consecutives heart beats HB is a direct frequency estimator. In one embodiment, when the first indicator $I_1$ is below a predefined threshold, indicating a poor signal quality, the computation algorithm selected is a signal modeling algorithm. Said modelling algorithm may be a blind equalization algorithm, a MAP technique, the algorithm for modeling of an average signal or a Cyclo-stationarity feature detection or the like.

According to one embodiment, the method implements a succession of steps configured to automatically chose the optimal algorithm(s) to execute from the library, the level of confidence associated to the results of the chosen algorithm(s) and the method to implement in order to combine the outputs of said algorithm(s).

According to one embodiment, the method according to the first aspect of the present invention comprises a step of estimation EST1 of the heart rate HR and/or the respiratory rate RR.

According to this embodiment, the average heart rate HR and/or the average respiratory rate RR are estimated from the calculated breath cycle BC and/or time interval separating two consecutive heart beat HB. In one preferred embodiment, the heart rate HR and/or the respiratory rate RR are obtained by the fusion of the breath cycle and/or the time interval separating two consecutive heart beats estimated on each of the axis of the orientation vector which are obtained with at least one algorithm. This fusion can be performed according to several techniques including Kalman filtering, weighted average techniques and/or maximum likelihood-based approaches and/or the like.

In one embodiment, the method according to the first aspect of the present invention comprises an estimation step EST2 consisting in the estimation of a quality metrics QM related to the accuracy of the heart rate HR and/or the respiratory rate RR estimated. According to one embodiment, the first indicator $I_1$ is calculated on the basis of said quality metrics QM. In one embodiment, the quality metric QM is the signal-to-noise ratio for each of the heart rate HR and/or the respiratory rate RR obtained by the at least one selected computation algorithm. Said signal-to-noise ratio being calculated as the comparison between the amounts of energy that are present in the useful frequency bands. In another embodiment, the quality metric QM is obtained from the heart rate HR and respiratory rate RR estimated in the frequency domain by finding a peak of high amplitude, the quality metric QM is computed in relation to the absolute height of the same peak. In another embodiment, the quality metric is obtained as the in inverse proportion of the absolute norm of the accelerometer signal $S_a$ and gyroscope signal $S_g$, so that signals obtained when the subject is moving are given a low quality index. In this embodiment, the quality metric QM, obtained at the estimation step EST2, may be calculated before the step of estimation EST1 of the heart rate HR and/or the respiratory rate RR and be directly used to calculate the first indicator $I_1$. More in general, whenever the quality metric QM is estimated from variable available before the step of estimation EST1 of the heart rate HR and/or the respiratory rate RR, the quality metric QM and first indicator $I_1$ may be directly estimated before the step of estimation EST1.

In one embodiment, the quality metric QM is obtained using a combination of methods, such as for example a combination of the methods described here above.

Multiple quality metric may be calculated to take into account both the unprocessed signal (i.e. signal to noise ratio of the raw signal) and the processed signal (i.e. evaluation of the dispersion of the processed signal).

According to one embodiment, the obtained quality metric QM is used as feedback for the different steps of the method.

In one embodiment, the obtained quality metric QM is used to update the filter coefficients according to an adaptive approach in which the pass-bands of the filters are progressively focused according to the latest estimated values of the heart rate HR and the respiratory rate RR. According to one embodiment, the update of the filter coefficient is performed as follows:
- the two pass band filters are each initialized in order to analyze a wide band of signals;
- when the quality matrix QM obtained is above a predefined threshold, the width of the filter band is iteratively reduced by a preset amount at each iteration;
- when the quality matrix QM obtained is below a predefined threshold, the width of the filter band is widened by a preset amount at each iteration to ensure that the useful signal has not been removed.

Advantageously, the method of the present invention provides a technical solution allowing the execution of signal processing algorithms by electronic systems having limited computational performances, as the ones that may be integrated in portable monitoring devices described here below.

A second aspect of the present invention relates to a method to evaluate of a heart rate HR and/or a respiratory rate RR of a subject wearing a monitoring device comprising at least one accelerometer, one gyroscope and one photoplethysmograph sensor. According to one embodiment, said monitoring device comprises a processor or a microprocessor to implement the steps of the method. This method is designed to reduce the energy consumption by optimizing the utilization time of the photoplethysmograph which is an energy consuming sensor. Energy consumption is further optimized by adapting the choice of the computation algorithms on the base of the quality of the acquired signal. The quality of the acquired signal is calculated in order to choose the more adequate algorithm to the situation.

Figure 2:
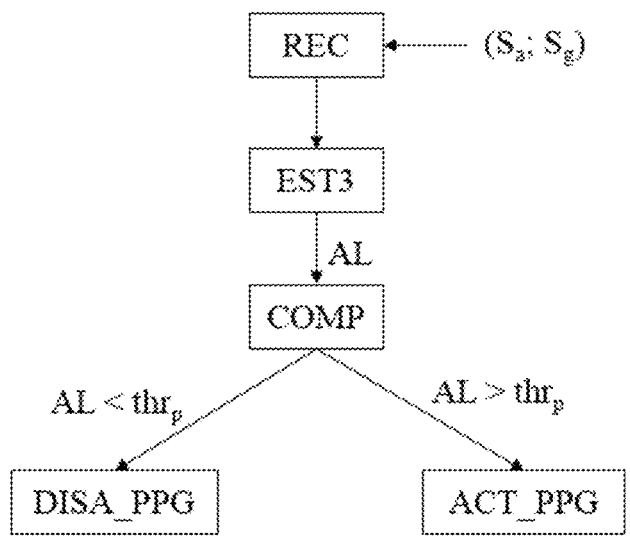
FIG. 2 is a flow chart showing the main steps of the method for the optimization of the battery consumption of the monitoring device according to one embodiment.

An exemplary illustration of the method according to the second aspect of the present invention is shown in FIG. 2.

The method, according to the second aspect of the present invention, comprises a preliminary step REC consisting in the reception of signals acquired by the at least one accelerometer $S_a$ and the at least one gyroscope $S_g$. In one alternative embodiment, said preliminary step further comprises the acquisition of the signals of the at least one accelerometer $S_a$ and the at least one gyroscope $S_g$.

In one embodiment, the method comprises an estimation step EST3 consisting in the estimation of an activity level AL parameter of the subject according to the signals acquired by the at least one accelerometer $S_a$ and the at least one gyroscope $S_g$. According to this embodiment, the at least one accelerometer $S_a$ and the at least one gyroscope $S_g$ are combined with the quaternion computation stage which outputs an orientation vector $V_o$. Said orientation vector $V_o$ is then passed thought a derivative calculator to quantify the amplitude of the current movements and estimate the activity level AL of the subject in order to discriminate between periods of low and high activity.

According to one illustrative example, a level of activity AL below the predefined threshold is associated to a period of rest of the subject (i.e. sleeping, resting on a sofa and the like) while a level of activity AL above the predefined threshold is associated to a period of activity (i.e. walking, running, stair-climbing and the like).

According to one embodiment, the method is configured to adapt the measurement rate of the PPG sensor according to the level of activity AL of the subject in order to reduce the energy consumption of the monitoring device. This adaptation is performed by reducing the acquisition rate of the PPG sensor during the subject rest period and by improving the acquisition rate of the PPG sensor during the subject activity period. For example, during sleep the monitoring device activates the PPG sensor each 15 minutes while during intense activity, such as running, the PPG sensor remains activated.

According to one embodiment, the acquisition rate of the PPG sensor is increased when anomalies are detected in the estimated heart rate HR and/or the respiratory rate RR.

According to one embodiment, the method is configured to activate the PPG sensor if the value of the quality metric QM relating to the measurement obtained by the inertial unit degrades below a predefined threshold.

According to one embodiment, the method according to the second aspect of the invention comprises a step of comparison COMP. In this embodiment, the activity level AL of the subject is compared to a predefined threshold. In one embedment, on the base of this comparison step COMP, the PPG sensor 2 is switched on or off. In one embodiment, the PPG sensor 2 is activated ACT_PPG when the activity level AL is above the predefined threshold. In this configuration the heart rate HR and/or the respiratory rate RR are calculated using the PPG signal $S_p$. In one alternative embodiment, the PPG sensor 2 is automatically activated when the variation of the heart rate HR and/or the respiratory rate RR is above a threshold. This embodiment enables to get $SpO_2$ when the variation of heart rate HR and respiratory rate RR exceed a predefined threshold during the rest period of the subject. According to one embodiment, the reliability of the heart rate HR and/or the respiratory rate RR estimations obtained from accelerometer signals $S_a$ and gyroscope signals $S_g$ is validated by correlating these results with breath rate HR and/or the respiratory rate RR derived from PPG sensor at rest.

According to one embodiment, the measurement rate of the PPG sensor is adapted in order to increase the measurement rate when the heart rate HR and/or the respiratory rate RR exceed the predefined threshold. This will help medical staff and physicians to better diagnose the patient status.

Alternative methods to extract the heart rate HR and/or the respiratory rate RR from the PPG signal $S_p$ are known by the man skilled in the art.

In one embodiment, the PPG sensor is disactivated DIS-A_PPG when the level of activity AL is below the predefined threshold. In this configuration the method to estimate the heart rate HR and/or the respiratory rate RR from accelerometer signal $S_a$ and gyroscope signal $S_g$ is implemented according to the embodiment here above.

According to one embodiment, the PPG sensor is periodically activated even during low activity periods of the subject during which the gyroscope and the accelerometer are used for heart rate HR and/or the respiratory rate RR estimation. The PPG signal $S_p$ is then used to evaluated the accuracy of the heart rate HR and/or the respiratory rate RR estimation obtained from the method using inertial motion unit signals only.

According to one embodiment, the difference of estimation obtained from the PPG signal $S_p$ and inertial motion unit signals are used as feedback signal for the calculation of the filter coefficients.

According to one embodiment, the preliminary step REC further consists in the reception of signals acquired by the at least one temperature sensor put in close proximity to the skin of the subject so as to measure skin temperature. The temperature measurements, taken alone or in combination with the measures cited here above, may be used to control the activation rate of the PPG sensor. The temperature sensor allows to detect the decrease of the temperature of the skin below a predeterminate threshold (i.e. 25° C.) in which case the tissues present underperfusion. Indeed, in case of low blood perfusion, the PPG sensor does not able to provide a signal of good quality due to the fact that cardiac and respiratory modulation are less visible. In those cases, the PPG sensor remains disactivated and only the accelerometer $S_a$ and the gyroscope $S_g$ are activated to acquire motion signals. According to another example, the method is configured so that when a large variation in temperature is detected, for example due to an intense physical activity or a health issue, the PPG sensor is activated to accurately detect the heart rate HR, a respiratory rate RR and/or $SpO_2$ of the subject. According to another example, the temperature sensor is used to determine if the monitoring device is actually worn by the subject or not and so as to maintained disactivated the PPG sensor and the inertial motion unit when the device is not worn.

In one embodiment of the present invention, the method further comprises computational steps to implement a motion artifact suppression method wherein the signals obtained from the accelerometer $S_a$ and gyroscope $S_g$ are used to estimate the noise on the PPG signal $S_g$ and remove it from the latter. The man skilled in the art knows several methods to remove motion artifact from PPG signal $S_p$ using accelerometer signals $S_a$ and gyroscope signal $S_g$. However, the techniques of the prior art merely rely on estimating the frequency of walking in order to filter the corresponding frequency on the PPG signal $S_p$. These techniques are therefore not able to fully remove the motion artifacts, in particular, they are not able to properly estimate and remove noise caused by sporadic non-periodic movements. The solution proposed herein differs from these prior techniques since it allows to accurately estimate the transfer function between the orientation vector signal and the PPG noise component in the signal. In one embodiment, the motion artifact suppression method comprises a step consisting in reconstructing an interfering motion signal and subtracting said interfering motion signal in the time domain from the PPG signal $S_p$, according to a method called Serial Interference Cancellation. According to this method, the interference signal is removed from the PPG signal. According to one embodiment, the quality of interference removal is constantly estimated by measuring how close the cleaned signal is to its expected signal profile. Said expected signal profile is obtained thanks to the average signal of a heart beat HB and/or breath cycle BC computed by the estimation stage depicted earlier.

A third aspect of the present invention relates to a monitoring device 1 for monitoring a physiological parameter of a subject wearing said monitoring device 1. According to one embodiment, the monitoring device 1 comprises at least a photoplethysmograph 2 also called herein PPG sensor, to measure oxygen saturation in blood in order to detect a frequency related to hearth rate HR and respiratory rate RR, and an inertial motion unit (IMU) 3 comprising at least one gyroscope and/or at least one accelerometer.

According to one embodiment, the monitoring device 1 further comprises a temperature sensor 4 for monitoring skin temperature.

In one embodiment the PPG sensor 2 includes a periodic light source, a photo-detector positioned to receive periodic light emitted by the periodic light source after interacting with a user's skin, and a circuitry determining a user's heart rate HR and respiratory rate RR from an output of the photo detector. In some embodiments, the periodic light source includes two periodic light sources straddling the photo-detector. In some embodiments, the photoplethysmographic sensor 2 further includes a housing having a recess in which the photo detector is disposed. In some embodiments, the housing of the photoplethysmographic sensor 2 further includes a second recess in which the periodic light source is disposed.

Figure 4:
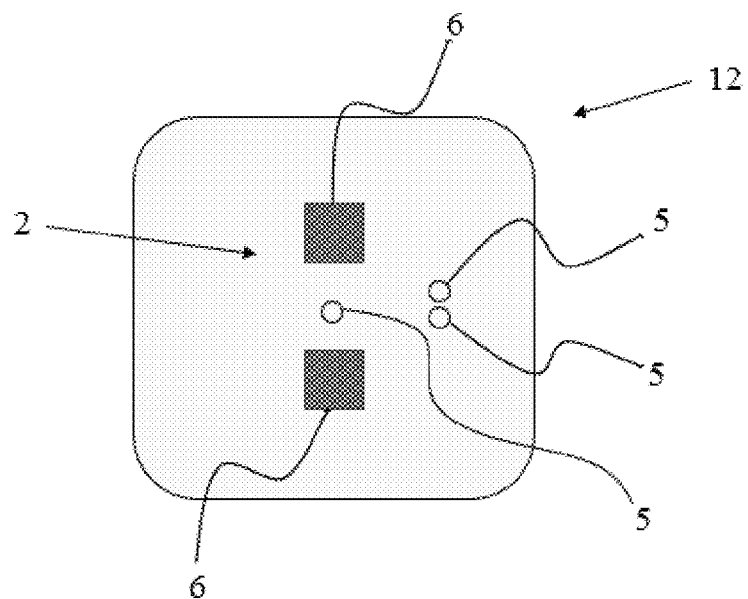
FIG. 4 is a schematic representation of the components (5, 6) of the PPG sensor 2 displacement on the skin-side of the monitoring device housing 12 according to one embodiment.

In one embodiment, the periodic light source 5 of the PPG sensor 2 is at least one LED. In one preferred embodiment, the PPG sensor 2 comprises at least two LEDs, notably three LEDs (see FIG. 4), emitting at the same wavelength or emitting at different wavelengths having different depths of penetration in tissues (e.g. wavelength corresponding to red, green, infrared, yellow). The use of multiple light sources having different positions and/or emitting light at different wavelengths has the advantage of providing multiple different measures, due to the not identical optical paths for the different LEDs resulting from the different positions and/or the different depths of penetration, and therefore providing multiple estimations of the parameters of interest, which are used to obtain a more robust evaluation of a heart rate HR, a respiratory rate RR and/or $SpO_2$ of the subject. According to one embodiment, the inertial motion unit 3 has 6-axis.

Figure 3:
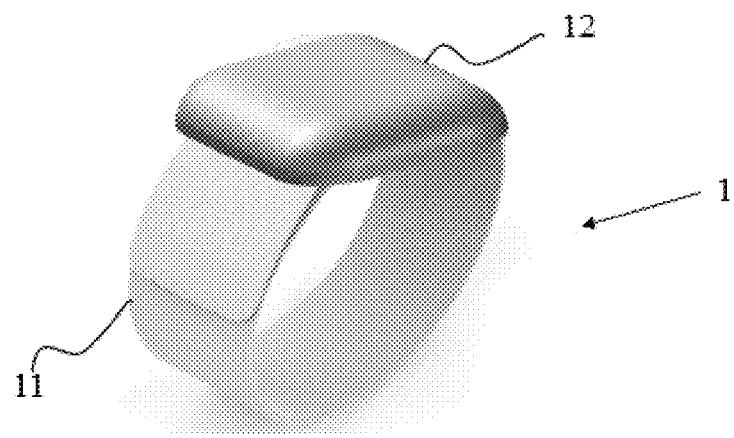
FIG. 3 is a schematic representation of the monitoring device 1 according to one embodiment wherein the monitoring device housing 12 is fixed on a wristband 11.
Figure 7:
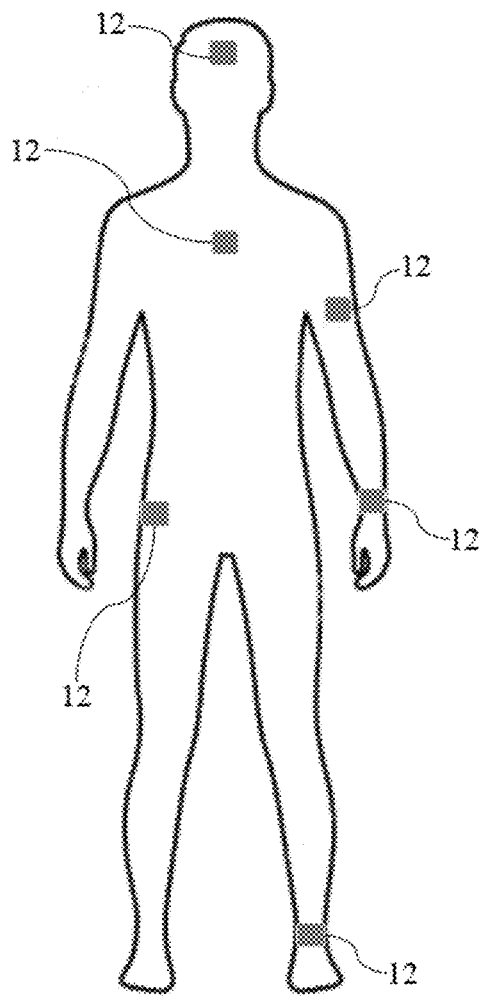
FIG. 7 is a schematic representation of the possible emplacement of the monitoring device housing 12 on the subject body.

For example, in one illustrative embodiment, the light source(s) 5 and/or associated photo-detector(s) 6 of the PPG sensor 2 may be disposed on band made of a flexible or pliable substrate. The PPG sensor 2 may be positioned on the band in order to be on the skin-side of a wristband (FIG. 3). The flexibility of band substrate allows the PPG sensor 2 to be positioned close to the skin of the subject (i.e., with little to no gap between the skin-side of the device and the adjacent surface of the skin of the subject. The band 11 may be made of a compliant material, to conform to the shape of the body part (for example, the user's wrist, arm, ankle, and/or leg) to which the monitoring device is coupled to or attached during monitoring so that the light source(s) and/or associated detector(s) are/is close or adjacent to the skin of the subject. As illustrated in FIG. 7, according to one embodiment, the shape and dimension of the band 11 are adapted to place the monitoring device housing 12 close or adjacent to the subject skin at the wrist, the arm, the torso, the forehead, the ankle, the leg or the hip. In order to clarify the drawings, the bands 11 associated to each monitoring device housing 12 pictured are not represented.

Figure 5:
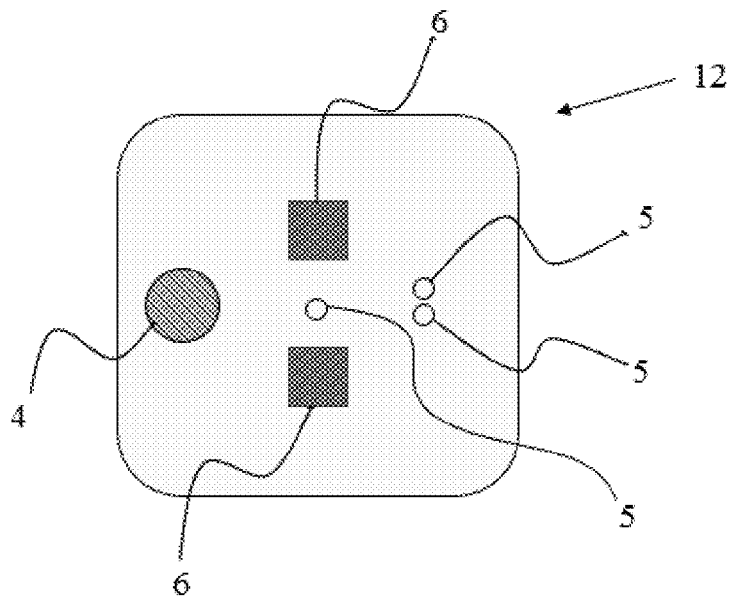
FIG. 5 is a schematic representation of the components (5, 6) of the PPG sensor 2 displacement and temperature sensor 4 displacement on the skin-side of the monitoring device housing 12 according to one embodiment.
Figure 6:
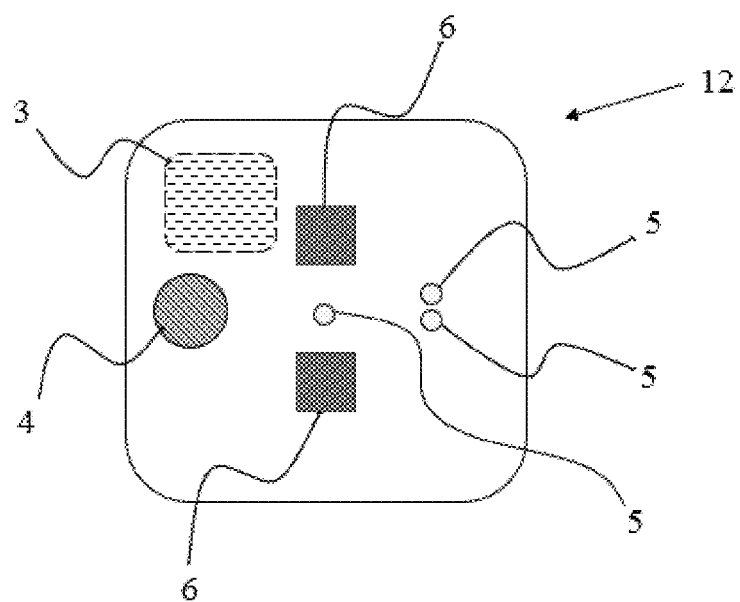
FIG. 6 is a transparent view of the monitoring device housing 12 according to one embodiment, wherein the inertial motion unit 3 comprised inside the monitoring device housing 12 is shown by dashed contouring.

In a preferred embodiment, the monitoring device comprising the PPG sensor 2, the inertial motion unit 3 and the skin temperature sensor 4 are comprised in a housing 12 fixed on a wristband 11 to be positioned on a wrist of the subject as illustrated in FIGS. 5 and 6. In one embodiment, the inertial motion unit 3 is entirely comprised inside the housing 12 and is not visible on the external surface of the housing 12 (i.e. the inertial motion unit 3 is represented in dashed lines in FIG. 6 which is a view in transparence of the skin-side of the housing 12).

In one embodiment, the monitoring device 1 is configured to perform features and operations associated with various methods described elsewhere herein to evaluate of a heart rate HR and/or a respiratory rate RR of a subject.

The advantage of a monitoring device and methods as disclosed in the present invention, is that they allow to monitor the heart and respiratory rate of a subject on extended time periods (i.e. from a few hours to a few days) thanks to the energy saving methods implemented. Moreover, the design of the device and methods implemented allows to retrieve high quality signals no matter the position of the monitoring device on the subject body (i.e. the wrist, the arm, the torso, the forehead, the ankle, the leg or the hip).

According to one embodiment, the monitoring device 1 comprises a processor and a computer-readable memory. Possible implementations of the processor include a microprocessor and a controller. The computer-readable memory may be volatile, non-volatile, or a combination thereof.

In one embodiment, data acquired by the monitoring device 1 are transmitted in any suitable manner to (and controlled by) an external device or system. In one exemplary embodiment of the present invention, the monitoring device data is transmitted to an intermediary companion device. Said companion device may be implemented in a variety of ways, including a smartphone, a tablet computer, a notebook computer and the like. Data may be transmitted in parallel or in sequence, raw or processed. In some embodiments, the monitoring device 1 also includes wireless networking hardware (e.g., a WiFi chipset or a cellular baseband chipset), through which the wearable device communicates with other devices over networks such as WiFi networks or cellular networks.

According to one embodiment, several components are communicatively linked to the monitoring device processor, including short-range wireless hardware (e.g., a Bluetooth® chip set or a near-field communication chip), a memory, a display, and user input devices (e.g., a capacitive touch screen, microphones, and physical buttons). The processor transmits data to and receives data from monitoring device 1 via the short range wireless hardware. In some embodiments, the companion device includes wireless networking hardware. Each component may have its own power supply or a central power source may supply power to one or more of the components of the device.

Some embodiments of the invention operate in a networked environment, which can include a network. The network can be any type of network familiar to those skilled in the art that can support data communications using any of a variety of commercially available protocols, including without limitation TCP/IP, SNA, I PX, AppleTalk, and the like. Merely by way of example, the network can be a local area network ("LAN"), including without, limitation an Ethernet network, a Token-Ring network and/or the like; a wide-area network (WAN); a virtual network, including without limitation a virtual private network ("VPN"); the Internet; an intranet; an extranet; a public switched telephone network ("PSTN"); an infrared network; a wireless network, including without limitation a network operating under any of the IEEE 802.11 suite of protocols, the Bluetooth™ protocol known in the art, and/or any other wireless protocol; and/or any combination of these and/or other networks.

Embodiments of the invention can include one or more server computers which can be co-located with the monitoring device 1 or the companion device, or remotely, for example, in the "cloud". Each of the server computers may be configured with an operating system, including without limitation any of those discussed above, as well as any commercially (or freely) available server operating systems. Each of the servers may also be running one or more applications and databases, which can be configured to provide services to the monitoring device 1 directly, one or more intermediate companion devices, and/or other servers. In a preferred embodiment, the server is configured to comply with regulations on health data hosting.

According to one embodiment, the devices and methods described here are implemented in a computing system that includes a back end component (e.g., as a data server), or that includes a middleware component (e.g., an application server), or that includes a front end component (e.g., a companion device having a graphical user interface or a Web browser through which a user can interact with an implementation of the devices and methods described here), or any combination of such back end, middleware, or front end components. In one exemplary embodiment, the web browser is configured to graphically represent cardio-respiratory data acquired with the monitoring device 1, being available for the user of the monitoring device or for at least member of a medical staff.

According to one embodiment, the computer readable program code for carrying out operations for methods of the present invention may be written in any combination of one or more programming languages, including an object oriented programming language such as Java, Python, Ruby, PHP, C++ or the like and conventional procedural programming languages, such as the "C" programming language or similar programming languages. The computer readable program code may execute entirely on the monitoring device processor, partly on the device processor, as a stand-alone software package, partly on the device processor and partly on a remote computer or entirely on the remote computer or server. In the latter scenario, the remote computer may be connected to the device processor through any type of network, including a local area network (LAN) or a wide area network (WAN), or the connection may be made to an external computer (for example, through the Internet using an Internet Service Provider).

The computer readable program code may also be stored in a computer readable medium that can direct a computer, other programmable data processing apparatus, or other devices to function in a particular manner, such that the instructions stored in the computer readable medium produce an article of manufacture including instructions which implement the function/act specified in the schematic flowchart diagrams and/or schematic block diagrams block or blocks.

The computer readable program code may also be loaded onto a computer, other programmable data processing apparatus such as a tablet or phone, or other devices to cause a series of operational steps to be performed on the computer, other programmable apparatus or other devices to produce a computer implemented process such that the program code which execute on the computer or other programmable apparatus provide processes for implementing the functions/acts specified in the flowchart and/or block diagram block or blocks.

While various embodiments have been described and illustrated, the detailed description is not to be construed as being limited hereto. Various modifications can be made to the embodiments by those skilled in the art without departing from the true spirit and scope of the disclosure as defined by the claims.

The invention claimed is:

1. A method to evaluate a heart rate and/or a respiratory rate of a subject wearing a monitoring device comprising at least one accelerometer, at least one gyroscope, at least one photoplethysmograph, and a processor comprising a microprocessor and a controller, wherein said method comprises the following steps:

estimating, by the processor, a level of activity of the subject according to signals acquired by the at least one accelerometer and the at least one gyroscope;

comparing, by the processor, said level of activity to a predefined threshold; and either:

if the photoplethysmograph is in a deactivated state, activating, by the processor, the photoplethysmograph, or activating, by the processor, the photoplethysmograph and maintaining, by the processor, the photoplethysmography in an activated state when the level of activity is above the predefined threshold and calculating, by the processor, the heart rate and/or the respiratory rate using the photoplethysmographic signal; or if the photoplethysmograph is in an activated state, deactivating, by the processor, the photoplethysmograph, or deactivating, by the processor, the photoplethysmograph and maintaining, by the processor, the photoplethysmograph in a deactivated state when the level of activity is below the predefined threshold and implementing, by the processor, a method to monitor physiological signals by processing signals acquired with at least one accelerometer and one gyroscope for the evaluation of a heart rate and/or a respiratory rate of a subject wearing a monitoring device comprising said accelerometer, said gyroscope, and the processor, said method comprising the following steps:

receiving, by the processor, the signals acquired by the accelerometer and the gyroscope with a predefined sampling frequency at n sampling times in a given time window, so as to obtain a pair of n successive samples of the signals acquired by the accelerometer and the gyroscope in the given time window;

for each pair of the n successive samples of the signals acquired by the accelerometer and the gyroscope in the given time window, combining, by the processor, the n successive samples of the signals of the accelerometer and the gyroscope, by the processor using a quaternion representation so as to output an orientation vector for each n sampling time, the processor using the quaternion representation providing computational simplicity and increased power efficiency, wherein the orientation vectors for all n sampling times in the given time window collectively define an orientation signal;

applying, by the processor, at least one filter to the orientation signal so as to obtain a filtered signal for the given time window;

calculating, by the processor, an average breath cycle and/or an average time interval separating two consecutive heart beats, the processor using an algorithm for modeling an average signal, said algorithm iteratively determining said average breath cycle and/or said average time interval separating two consecutive heart beats by computing an average signal between the filtered signal obtained for the given time window and an average signal obtained in a preceding iteration for a preceding time window;

estimating, by the processor, a heart rate and a respiratory rate from the average breath cycle and the average time interval separating two consecutive heart beats calculated; and transmitting, by the processor, data to a companion device or a server operating system, said data selected from the group consisting of: the pair of n successive samples of signals, the average breath cycle and/or the average time interval separating two consecutive heart beats calculated, the heart rate and/or the respiratory rate estimated, and combinations thereof, wherein the deactivating, by the processor, of the photoplethysmograph when the level of activity reduces energy consumption of the monitoring device.

2. The method according to claim 1, wherein the photoplethysmograph is periodically activated, by the processor, and the heart rate and/or the respiratory rate estimated with the PPG signal are used to evaluate, by the processor, the heart rate and/or the respiratory rate obtained signals acquired with at least one accelerometer and one gyroscope.

3. The method according to claim 2, wherein the difference between the heart rate and/or the respiratory rate obtained from the photoplethysmographic signal and the at least one accelerometer and one gyroscope signal is used as feedback signal for the calculation of the filter coefficients by the processor.

4. The method according to claim 1, further comprises a step for removing, by the processor, a motion artefact from the photoplethysmographic signal.

5. The method according to claim 1, wherein the method to monitor physiological signals by processing signals acquired with at least one accelerometer and one gyroscope further comprises a step of estimating, by the processor, a quality metrics related to the accuracy of the heart rate and/or the respiratory rate estimated and a step of calculating, by the processor, filter coefficients of the at least one filter on the basis of said quality metrics.

6. The method according to claim 5, wherein the average breath cycle and/or the average time interval separating two consecutive heart beats are further calculated, by the processor, using at least one computation algorithm chosen from a list comprising at least a direct frequency estimation algorithm and a blind equalization algorithm, the selection of the computing algorithm being made on the basis of at least one first indicator calculated from said quality metrics.

7. The method according to claim 5, wherein the step of applying the at least one filter to the orientation signal comprises the application of two band pass filters optimized according to a Parks-Mcclellan method.

8. The method according to claim 1, wherein the step of applying the at least one filter comprises:
   filtering, by the processor, the orientation signal in the band [0.08 Hz; 0.5 Hz] for selecting a part of the orientation signal comprising at least partially the breath activity; and
   filtering, by the processor, the orientation signal in the band [0.5 Hz; 4 Hz] for selecting a part of the orientation signal comprising at least partially the heart activity.

9. A monitoring device for monitoring a physiological parameter of a subject wearing said monitoring device, comprising:
   a photoplethysmograph, to measure oxygen saturation in blood in order to detect a frequency related to hearth rate and respiratory rate;
   an inertial motion unit comprising at least one gyroscope and/or at least one accelerometer; and
   a processor comprising a microprocessor and control, the processor being configured to implement the following steps:
      measuring a level of activity of the subject according to signals acquired by the at least one accelerometer and the at least one gyroscope;
      comparing said level of activity to a predefined threshold; and either:
         if the photoplethysmograph is in a deactivated state, activating the photoplethysmograph, by the processor, or activating the photoplethysmograph, by the processor, and maintaining, by the processor, the photoplethysmorgraph in an activated state when the level of activity is above the predefined threshold and calculating, by the processor, the heart rate and/or the respiratory rate using the photoplethysmographic signal; or
         if the photoplethysmograph is in an activated state, deactivating the photoplethysmograph and implementing, by the processor, a method to monitor physiological signals by processing signals acquired with at least one accelerometer and one gyroscope for the evaluation of a heart rate and/or a respiratory rate of a subject wearing a monitoring device comprising said accelerometer, said gyroscope, and the processor, said method comprising the following steps:
            receiving, by the processor, the signals acquired by the accelerometer and the gyroscope with a predefined sampling frequency at n sampling times in a given time window, so as to obtain a pair of n successive samples of the signals acquired by the accelerometer and the gyroscope in the given time window;
            for each pair of the n successive samples of the signals acquired by the accelerometer and the gyroscope in the given time window, combining, by the processor, the n successive samples of the signals of the accelerometer and the gyroscope, by the processor using a quaternion representation so as to output an orientation vector for each n sampling time, the processor using the quaternion representation providing computational simplicity and increased power efficiency, wherein the orientation vectors for all n sampling times in the given time window collectively define an orientation signal;
            applying, by the processor, at least one filter to the orientation signal so as to obtain a filtered signal for the given time window;
            calculating, by the processor, an average breath cycle and/or an average time interval separating two consecutive heart beats, the processor using an algorithm for modeling an average signal, said algorithm iteratively determining said average breath cycle and/or said average time interval separating two consecutive heart beats by computing an average signal between the filtered signal obtained for the given time window and an average signal obtained in a preceding iteration for a preceding time window;
            estimating, by the processor, a heart rate and a respiratory rate from the average breath cycle and the average time interval separating two consecutive heart beats calculated; and
            transmitting, by the processor, data to a companion device or a server operating system, said data selected from the group consisting of: the pair of n successive samples of signals, the average breath cycle and/or the average time interval separating two consecutive heart beats calculated, the heart rate and/or the respiratory rate estimated, and combinations thereof,
   wherein the activating, by the processor, of the photoplethysmograph when the level of activity is above a predefined threshold reduces energy consumption of the monitoring device.

10. The monitoring device according to claim 9, further comprising a temperature sensor.

11. The monitoring device according to claim 9, wherein the data acquired and/or processed by the monitoring device are transmitted to the server operating system.

12. The monitoring device according to claim 9, wherein the data acquired and/or processed by the monitoring device are transmitted to the companion device.

13. The monitoring device according to claim 9, wherein the method to monitor physiological signals by processing signals acquired with at least one accelerometer and one gyroscope further comprises a step of estimating, by the processor, a quality metrics related to the accuracy of the heart rate and/or the respiratory rate estimated and a step of calculating, by the processor, filter coefficients of the at least one filter on the basis of said quality metrics.

14. The monitoring device according to claim 13, wherein the average breath cycle and/or the average time interval separating two consecutive heart beats are further calculated, by the processor, using at least one computation algorithm chosen from a list comprising at least a direct frequency estimation algorithm and a blind equalization algorithm, the selection of the computing algorithm being made on the basis of at least one first indicator calculated from said quality metrics.

15. The monitoring device according to claim 13, wherein the step of applying the at least one filter to the orientation signal comprises the application of two band pass filters optimized according to a Parks-Mcclellan method.

16. The monitoring device according to claim 9, wherein the step of applying the at least one filter comprises:
- filtering, by the processor, the orientation signal in the band [0.08 Hz; 0.5 Hz] for selecting a part of the orientation signal comprising at least partially the breath activity; and
- filtering, by the processor, the orientation signal in the band [0.5 Hz; 4 Hz] for selecting a part of the orientation signal comprising at least partially the heart activity.

17. A monitoring device for monitoring a physiological parameter, comprising:
- a photoplethysmograph, to measure oxygen saturation in blood in order to detect a frequency related to hearth rate and respiratory rate;
- an inertial motion unit comprising at least one gyroscope and/or at least one accelerometer; and
- a processor configured to implement the method according to claim 1.

\* \* \* \* \*